US00PP13675P29

(12) United States Plant Patent
Plevier

(10) Patent No.: US PP13,675 P2
(45) Date of Patent: Mar. 25, 2003

(54) ALSTROEMERIA PLANT NAMED 'ZANYSIA'

(75) Inventor: F. B. Plevier, Sassenheim (NL)

(73) Assignee: Van Zanten Plants B.V. (NL)

( * ) Notice: Subject to any disclaimer, the term of this patent is extended or adjusted under 35 U.S.C. 154(b) by 0 days.

(21) Appl. No.: 09/640,813

(22) Filed: Aug. 16, 2000

(51) Int. Cl.[7] ..... A01H 5/00
(52) U.S. Cl. ..... Plt./309
(58) Field of Search ..... Plt./309

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new and distinct Alstroemeria plant variety producing flowers of attractive coloration.

1 Drawing Sheet

CLASSIFICATION

The present invention relates to a new Alstroemeria sp. plant, in the family Amaryllidaceae.

VARIETY DENOMINATION

The new Alstroemeria sp. plant has the varietal denomination 'Zanysia'.

BACKGROUND OF THE INVENTION

The present invention relates to a new and distinct variety of Alstroemeria which is a cross of two unnamed, undistributed seedlings; namely, 394-002 as seed parent and HA08 as pollen parent. The 'Zanysia' hybrid was produced as a seedling in a research station in Rijsenhout, the Netherlands, and combines the quality and production of the seed parent with the flower color of the pollen parent.

Asexual reproduction by dividing rhizomes, and by tissue culture, through successive generations in Rijsenhout, The Netherlands, has demonstrated that the combination of characteristics as herein disclosed for 'Zanysia' are firmly fixed and retained through successive generations.

SUMMARY OF THE INVENTION

The new variety of Alstroemeria, 'Zanysia', produces attractive flowers.

DESCRIPTION OF ILLUSTRATION

The new variety of Alstroemeria hybrid is illustrated in the accompanying illustration, which shows typical flower characteristics, with colors being as nearly true as is possible for illustrations of this type. The photographic illustration submitted with this Application is a detail of flower stems of the new variety.

DETAILED DESCRIPTION OF THE NEW VARIETY

The following is a detailed description of the new cultivar of Alstroemeria hybrid as observed in a greenhouse in Rijsenhout, The Netherlands. The plant described is a 1-year old plant of the new variety grown in a greenhouse in The Netherlands. Color designations indicated are in accordance with The Royal Horticultural Society Colour Chart by color plate designations.

'Zanysia' has not been observed under all possible environmental conditions. Phenotypic expression may vary with variations in environment such as temperature, light intensity, day length and growing and cultural conditions.

Plant:
- *Form.*—Bush.
- *Shape.*—Upright.
- *Height.*—About 120 to 160 cm.
- *Growth rate.*—Medium.
- *Flowering stage.*—Length of time (number of days) taken from young rooted rootstocks (stage of development in which the varieties are sold) to flowering stage in commercial greenhouse conditions is about 90 to 110 days.
- *Pinching.*—Not required.

Stem:
- *Main stem or cain length.*—About 140 cm.
- *Internode length.*—About 2 to 10 cm.
- *Growth.*—Vigorous.
- *Strength.*—Strong.
- *Quantity.*—About 170 to 190 harvestable stems per $m^2$.

Lateral branches:
- *Average number.*—About 170 to 190.
- *Color.*—Near 141A.
- *Length.*—About 140 to 180 cm.
- *Diameter.*—About 0.5 to 1.2 cm.
- *Texture.*—Smooth.

Foliage:
- *Quantity.*—Abundant.
- *Number of leaves.*—About 15 to 30 per stem.
- *Size of leaf.*—Length about 2 to 20 cm; width about 0.5 to 3 cm.
- *Shape of leaf.*—Elliptic.
- *Margin type.*—Minutely crimped.
- *Texture.*—Leathery.
- *Color.*—Upperside near 141A; underside near 141A.
- *Phyllotaxy.*—Asymmetrical single.
- *Venation pattern.*—Parallel.
- *Color.*—Near 143A.
- *Points of attachment.*—Sessile.

Other plant characteristics:
- *Thorns.*—No.
- *Spines.*—No.
- *Prickles.*—No.
- *Bulbs.*—No.

*Corms.*—No.
*Rhizomes.*—Yes. Color: Near 155B. Size: About 10 to 30 cm.
*Disease resistance.*—Unknown.
*Fragrance.*—None.

INFLORESCENCE—FLOWER/FLORET

Blooming habit: Continuous, with no need to pinch spent umbels to maintain continuous blooming condition.
Blooms:
*Abundance.*—Blooms profusely throughout the year.
*Discoloration after full bloom.*—None.
*Effect of wet or hot weather.*—None.
*Persistence* (*do flowers hang on and dry*).—No.
Flower size: Medium, measured at stage of development when first anthers release their pollen.
*Diameter.*—About 7 cm.
*Depth.*—About 6 cm.
Borne: Singly.
Shape or form:
*When bloom first opens.*—Cup.
*When bloom matures.*—Cup.
Petalage:
*Number of petals.*—6.
*Arrangement.*—Two concentric circles of 3 petals.
*Form of tepals.*—Obovate.
*Margin type.*—Minutely crimped.
*Apex.*—Pointed.
*Duration of tepals.*—Stay on stem about 3 weeks.
*Texture.*—Velvety.
*Appearance.*—Leathery.
Petal color:
*Outer petal.*—Body near 69A to 73A; base near 65D; reverse side near 65A.
*Inside petal.*—Body near 155D to 65A; base near 155D; reverse side near 155D to 65A.
*Spots.*—Outer petals (3): None. Inner lateral petals (2): About 15 to 25 spots, near 60A. Inner median petal: About 0 to 15 spots; near 60A.
Tepal color:
*When tepals first divide.*—Near 151A to 34C.
*When petals begin to unfurl.*—Near 151A to 34C.
Peduncle or flower stem:
*Length.*—About 1 to 4 cm.
*Color.*—Near 140A.
*Strength.*—Strong, erect.
*Upright.*—Yes.
*Hairy.*—No.
Other flower characteristics:
*Discoloration after full bloom.*—No.
*Effect of hot or wet weather.*—Not affected.
*Disease resistance.*—Unknown.
*Fragrance.*—None.
*Lasting quality.*—On plant about 3 weeks; as cut flower about 12 to 14 days.
Flower bud:
*Size.*—Diameter: About 1 cm.
*Depth or length: About* 0.5 to 4.5 cm.
*Form or shape.*—Pearshaped; long, not pointed.
*Rate of opening.*—Fast.

REPRODUCTIVE ORGANS

Stamen:
*Number.*—About 6.
*Arrangement.*—Side by side around the style.
Anthers:
*Size.*—About 5–10 mm.
*Color.*—Near 189A.
Filaments:
*Length.*—About 4–5 cm.
*Color.*—Near 55B.
Pollen:
*Color.*—Near 79A.
Pistil:
*Number.*—1.
Style:
*Length.*—About 4–5 cm.
*Color.*—Near 55B.
Stigma:
*Color.*—Near 55A.
Fruit:
*Fertile.*—Yes.
*Shape.*—Ovoid.
*Placentation.*—Parietal.
*Color at maturity.*—Near 163A.
*Size of fruit at maturity.*—About 1 to 1.5 cm.
*Seeds.*—Round.
*Color.*—Near 164A.

I claim:

1. A new and distinct Alstroemeria plant of the variety substantially as shown and described.

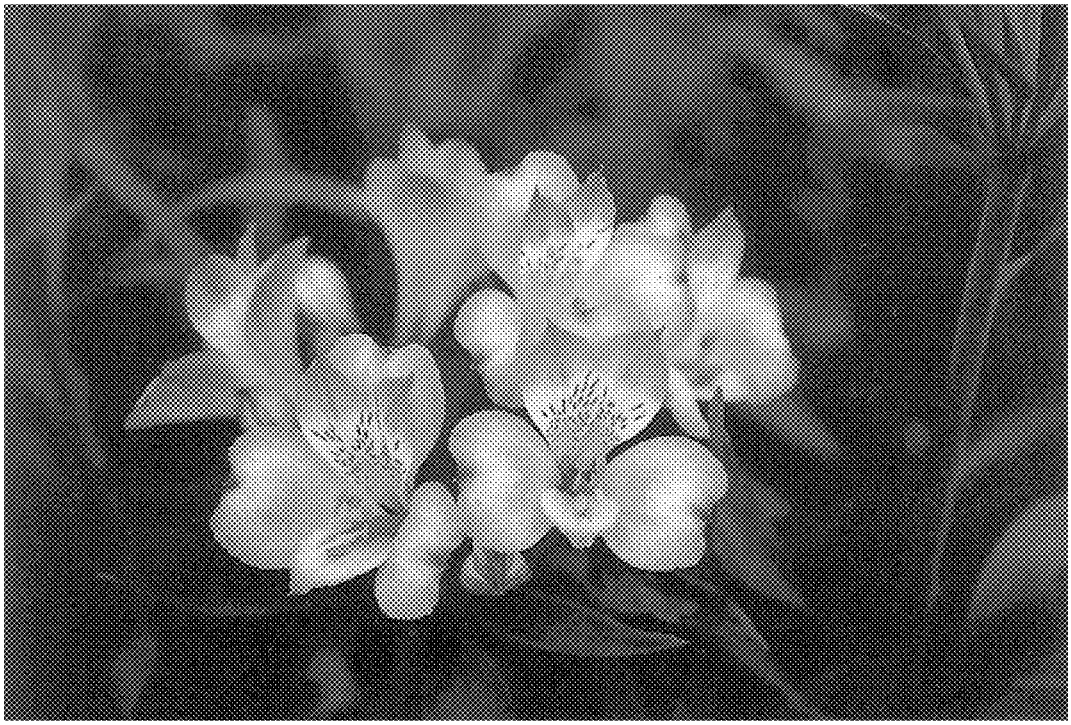

* * * * *